United States Patent
Varghese et al.

(10) Patent No.: US 7,297,116 B2
(45) Date of Patent: Nov. 20, 2007

(54) METHOD AND APPARATUS FOR IMAGING THE CERVIX AND UTERINE WALL

(75) Inventors: Tomy Varghese, Madison, WI (US); Mark Alan Kliewer, Madison, WI (US); James A. Zagzebski, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 892 days.

(21) Appl. No.: 10/420,125

(22) Filed: Apr. 21, 2003

(65) Prior Publication Data

US 2004/0210136 A1 Oct. 21, 2004

(51) Int. Cl.
*A61B 8/00* (2006.01)

(52) U.S. Cl. .................. 600/438; 600/443; 600/588
(58) Field of Classification Search ........ 600/437–438, 600/443, 447, 454–456, 588
See application file for complete search history.

(56) References Cited

U.S. PATENT DOCUMENTS

| | | | |
|---|---|---|---|
| 3,830,223 A * | 8/1974 | Beretsky et al. ............ | 600/443 |
| 4,349,033 A * | 9/1982 | Eden .......................... | 600/458 |
| 5,107,837 A | 4/1992 | Ophir et al. | |
| 5,178,147 A | 1/1993 | Ophir et al. | |
| 5,222,485 A * | 6/1993 | Jerath ......................... | 600/437 |
| 5,265,612 A | 11/1993 | Sarvazyan et al. | |
| 5,293,870 A | 3/1994 | Ophir et al. | |
| 6,450,963 B1 * | 9/2002 | Ackerman ................... | 600/459 |
| 2002/0068870 A1 | 6/2002 | Alam et al. | |

FOREIGN PATENT DOCUMENTS

EP 0 920 833 A1 9/1999
WO WO 01/06927 A1 2/2001

OTHER PUBLICATIONS

Ophir, et al., "Elastography: A Quantitative Method For Imaging The Elasticity of Biological Tissues", Ultrasonic Imaging 13, 111-134 (1991).
Kallel, Faouzi, et al., "The Feasibility of Elastographic Visualization of Hifu-Induced Thermal Lesions in Soft Tissues", Ultrasound in Med. & Biol., vol. 25, No. 4, pp. 641-647, 1999, World Federation for Ultrasound in Medicine & Biology.
Righetti, Raffaella, et al. Elastographic Characterization of Hifu-Induced Lesions in Canine Livers, Ultrasound in Med. & Biol., vol. 25, No. 7, pp. 1099-1113, 1999 World Federation for Ultrasound in Medicine & Biology.
Stafford, R. Jason, et al., "Elastographic Imaging of Thermal Lesions in Soft Tissue: A Preliminary Study of In Vitro", Ultrasound in Med. & Biol., vol. 24, No. 7, pp. 1449-1458, 1998, World Federation for Ultrasound in Medicine & Biology.
PCT International Search Report.

* cited by examiner

*Primary Examiner*—Francis J. Jaworski
(74) *Attorney, Agent, or Firm*—Boyle Fredrickson Newholm Stein & Gratz S.C.

(57) ABSTRACT

Elastography is used to examine soft tissue of the uterus to detect tumors and to evaluate the strength of the cervix of the uterus based on its elastographic properties.

38 Claims, 5 Drawing Sheets

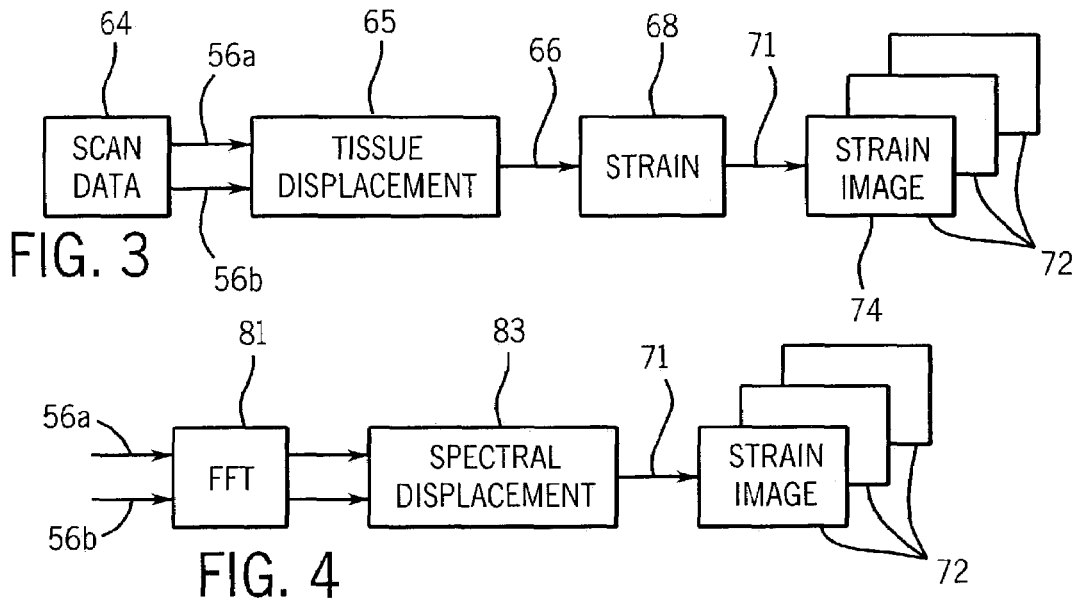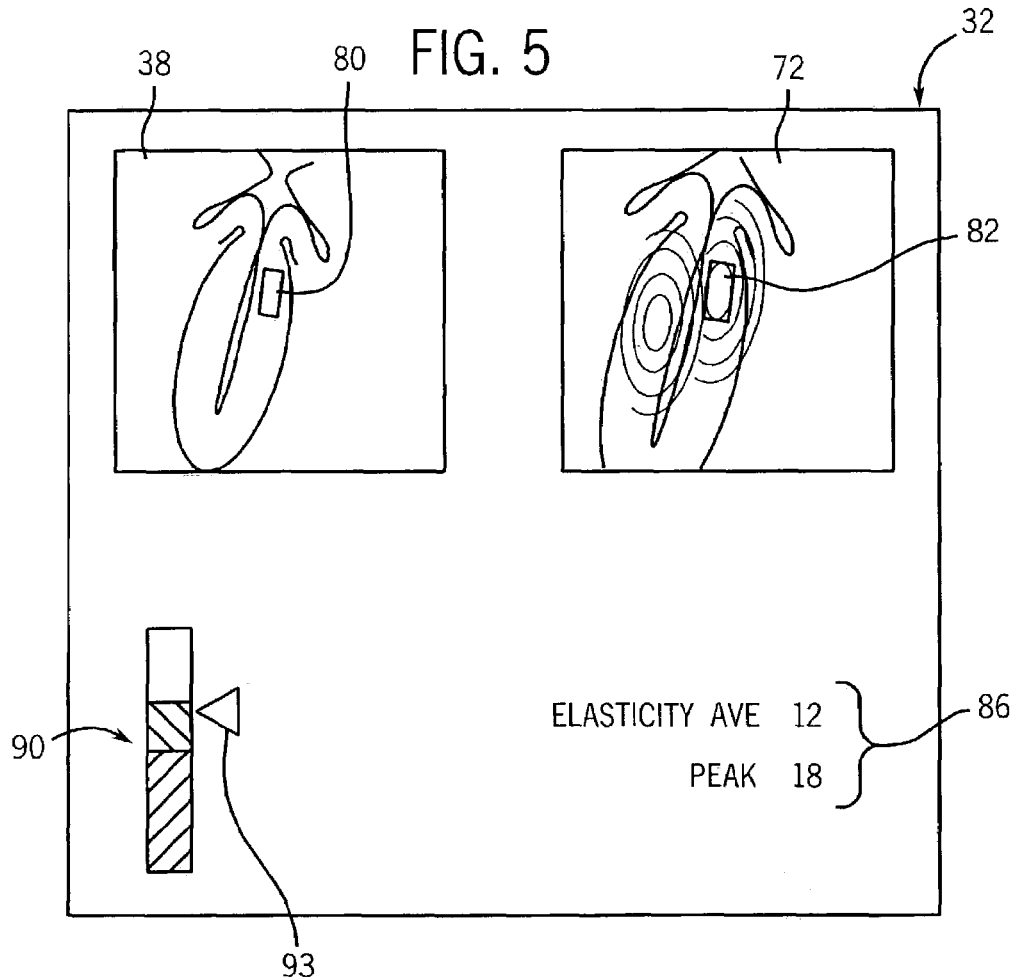

METHOD AND APPARATUS FOR IMAGING THE CERVIX AND UTERINE WALL

STATEMENT REGARDING FEDERALLY SPONSORED RESEARCH OR DEVELOPMENT

This invention was made with United States government support awarded by the following agencies: NIH CA 39224. The United States has certain rights in this invention.

CROSS-REFERENCE TO RELATED APPLICATIONS

--

BACKGROUND OF THE INVENTION

The present invention relates to a device for medical imaging and diagnosis and in particular for imaging methods suitable for examining the tissue of the uterus, cervix, and pelvic floor.

The uterus is a vase-like muscular organ the shape of an upside down pear about two and one-half inches long in non-pregnant women. The narrow neck of the uterus is called the cervix. An examination of the uterus is typically performed by touch (palpation) during which the physician explores the contours of the uterus and cervix using his or her fingers while pressing down on the abdomen. In this way, in some cases, the physician may detect tumors or cysts.

X-ray imaging methods, including computed tomography (CT), do not work well with the soft tissue of the uterus. Ultra-sound imaging may be employed, however, uterine fibroids and adenomyosis foci appear similar on conventional ultrasound scans making differentiation very difficult for the sonologist. Currently, magnetic resonance imaging (MRI) is the only imaging modality capable of characterizing these two conditions but MRI imaging is expensive, limiting its use as a screening tool.

Some problems with the uterus are manifest by postmenopausal bleeding which may be caused by a benign etiology (endometrial atrophy, hyperplasia, polyps, or leiomyomas). However, approximately 10-30% of women with menopausal bleeding will be found to have endometrial cancer. Distinguishing between these etiologies is difficult with current imaging technology.

Pre-term delivery is a complex problem that may result from incompetence of the cervix of the uterus. Although cervical incompetence is believed to be the principal causative factor in approximately 25% of miscarriages, it is difficult to determine which pregnancies might benefit from intervention and what the appropriate intervention might be. For example, the attending physician may recommend cerclage or simply prolonged bed rest.

A history of pre-term delivery may be used to estimate the chance of pre-term delivery or, alternatively, such a risk may be estimated from the length of the cervix usually measured with a trans-vaginal ultrasound image. However, cervical length has not proven to be a wholly reliable indicator of this condition.

Pelvic floor disorders, such as incontinence and prolapse, result from failure of the fibromuscular connective tissue sheath that forms the supporting structure for the organs of the deep pelvis. The identification of defects in this support structure is important for surgical planning and repair. At present, MRI imaging provides the only means of assessing these structures, but such imaging is expensive and available only in the larger centers.

BRIEF SUMMARY OF THE INVENTION

The present inventors propose the use of a new ultrasound technique termed elastography for assessment of uterine, cervical, and pelvic floor tissue. Elastography produces images closely related to tissue stiffness. When applied to the cervix, tissue stiffness may be an important factor in determining the competence of the cervix. Elastography may also allow differentiation between fibroids and adenomyosis in the uterine wall because adenomyosis is an ingrowth of soft, glandular endometrial tissue into the myometrium of the uterus, likely to be more flexible than fibroids, which are primarily composed of stiff fibrous tissues and muscular bundles and whorls. Further, it is believed that elastography may better highlight one of the features of uterine cancer, the relative rigidity of the neoplastic tissue. In this regard, elastography could distinguish diffuse, stiff endometrial tissue (cancer) from diffuse, soft endometrial tissue (hyperplasia), focal, stiff tissue (leiomyomas), and focal, soft tissue (polyps).

Specifically then, the present invention provides a method for evaluating the soft tissue of the uterus with respect to measurement of cervical incompetence using the steps of obtaining the first image of the cervix with an ultrasonic acoustic wave, then applying a displacement to the cervix after which a second image of the cervix is obtained to deduce elasticity of the cervix under the displacement. A measurement based on the deduced elasticity, indicating a likelihood of cervical incompetence, may then be output.

It is therefore one object of the invention to use an imaging modality that can provide a direct measurement of tissue elasticity of the cervix to evaluate cervical competence.

The displacement of the cervix and the imaging may both be performed by a single ultrasonic probe or a separate probe may be used for ultrasonic measurement and for displacement. In this latter case, the ultrasonic probe may be applied transabdominally. The probe for displacement may be a blunt rod or a balloon within the cervix.

Thus it is another object of the invention to provide an elastographic characterization of the cervix that may be employed flexibly with a variety of different techniques.

The output may be a comparison of the elasticity of the cervix with the threshold elasticity deduced from a standard population.

Thus it is another object of the invention to provide a simple measure of the risk of pre-term delivery.

The invention may include a step of defining an area of the cervical tissue and combining elasticity measurements over that area, and the output may be related to the combination of the elasticity measurements.

Thus it is another object of the invention to provide for a robust measurement system that uses multiple measurements over an area.

The same techniques of displacement and imaging may be applied to the uterus wall to detect and distinguish among abnormal masses. Specifically, a first image of the uterus may be obtained using an ultrasonic acoustic wave and a displacement applied to the uterus after which a second image of the uterus may be taken to deduce elasticity of the uterine wall. An image of the uterus may be produced indicating variations in elasticity associated with possible tumors.

Thus it is another object of the invention to allow differentiation among masses in the soft tissue of the uterus.

The same techniques of displacement and imaging may be applied to the fibromuscular tissues of the vaginal wall to detect pelvic floor defects. Specifically, a first image of the connective tissue sheath investing the vagina may be obtained using an ultrasonic acoustic wave and a displacement applied to the vaginal wall after which a second image of the uterus may be taken to deduce elasticity of the vaginal wall. An image of the vagina may be produced indicating variations in elasticity associated with possible connective tissue defects.

Thus it is another object of the invention to assess the integrity of the pelvic floor and allow identification of support defects in the pelvic floor.

In one embodiment of the invention, a specialized probe is used to evaluate uterine, cervical tissue or tissue of the pelvic floor, has a balloon sized for insertion into the relevant portion of the uterus or vagina to extend along its length and a pump communicating with the balloon to apply a controlled displacement of the uterine or cervical tissue by inflation of the balloon.

Thus it is one object of the invention to provide a localized and reproducible distention or compression of the tissue being examined.

The balloon may include an ultrasound transducer mounted within the balloon for acquiring images through the balloon into the uterine or cervical tissue.

Thus, it is another object of the invention to provide for improved and localized imaging of the tissue of the uterus.

In one embodiment of the invention, pressure or force sensors are used to measure the applied pressure. Pressure sensors on the transvaginal probe will be used to measure pressure when compression is applied to the cervix using the probe. Pressure measurements in the balloon will be performed when the pump and balloon is used to apply a controlled displacement of the uterine or cervical tissue by inflation of the balloon.

In one embodiment of the invention, pressure and strain measurements will be used to obtain quantitative or Young's Modulus values of the stiffness of the cervix and uterine tissue, using appropriate boundary conditions.

These particular objects and advantages may apply to only some embodiments falling within the claims and thus do not define the scope of the invention.

BRIEF DESCRIPTION OF THE DRAWINGS

FIG. 3 is a block diagram of the processing of the scan data of FIG. 2 by the ultrasound scanner of FIG. 1 to deduce stiffness using a time-domain analysis technique;

FIG. 4 is a figure similar to that of FIG. 3 using a frequency domain analysis technique;

FIG. 5 is a representation of the screen of the display of the apparatus of FIG. 1 showing juxtaposed conventional and strain tissue images and, showing tracking cursors for navigation and quantitative display of the strain measurement in numerical and graphical form;

DETAILED DESCRIPTION OF THE PREFERRED EMBODIMENT

Elastography is a known, but new imaging modality that reveals the stiffness properties of tissues, for example, axial strain, lateral strain, Poisson's ratio, Young's modulus, or other common strain and strain-related measurements. The strain measurements may be collected over an area and compiled as a two-dimensional array of data, which may then be mapped to a gray scale to form a strain "image".

In "quasi static" elastography, two conventional images of the tissue are obtained using ultrasound, computed tomography (CT), or magnetic resonance imaging (MRI). The first image provides a base line of the tissue at a given state of compression or distention and the second image is obtained with the tissue under a different compression or distention. The tissue may be compressed by an external agency such as a probe or the like or may be compressed by its own muscular action, for example, in the case of the heart, or by movement of adjacent organs. Displacement of the tissue between the two images is used to deduce the stiffness of the tissue. Quasi-static elastography is thus analogous to a physician's palpation of tissue in which the physician determines stiffness by pressing the tissue and detecting the amount that the tissue yields under this pressure.

In "dynamic" elastography, a low frequency vibration is applied to the tissue and the tissue vibrations accompanying the resulting elastic wave are measured, for example, using ultrasonic Doppler detection.

Figure 1:
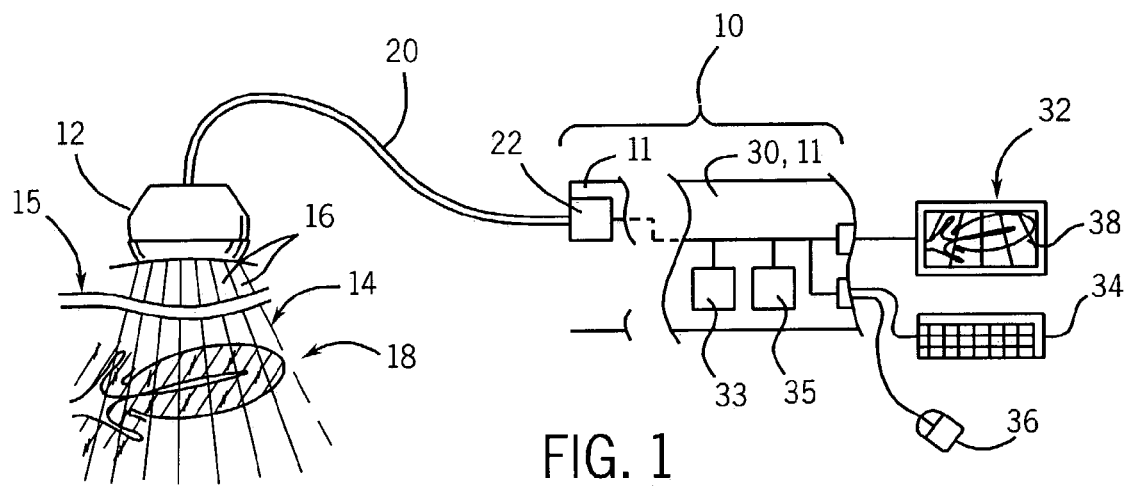
FIG. 1 is a simplified block diagram of an ultrasound scanner suitable for use with the present invention in scanning uterine tissue.

Referring now to FIG. 1, the present invention applies elastography to measurements of the uterus and cervix using an ultrasonic imaging system alone or in combination with a stand-alone computer 30. Generally, the ultrasonic imaging system 10 provides a graphic display 32, a keyboard 34 for data entry and a cursor control device 36, such as a mouse, as is well understood in the art for providing user input.

In a preferred embodiment, the ultrasonic imaging system 10 may make use of a Siemens Antares (commercially available from Siemens Medical Systems, Issaquah, Wash.) with a research interface or a GE Logiq 900 (commercially available from GE Medical Systems, Waukesha, Wis.) with a research interface ultrasound system communicating with a 3.5, 5 or 7.5 Megahertz linear or curvilinear array ultrasound transducer 12 transmitting and receiving a beam 14 of ultrasonic energy along a number of rays 16. For uterine imaging, as shown, the ultrasound transducer 12 may be placed against the patient's abdomen for transabdominal imaging. Alternatively, as described below, a transperineal or transvaginal probe of a type generally understood in the art may be used.

During data acquisition, the ultrasound transducer 12 transmits an ultrasound beam 14 toward the uterus 18 and receives echo data at each of numerous transducer elements. This data is transmitted via cable 20 to the ultrasonic imaging system 10 where it is received and processed by interface circuitry 22. Alternatively, echo data may be formed into signals representing echoes from along each of the rays 16 and then transmitted to ultrasonic imaging system 10. In the preferred embodiment, the data may be sampled at least 2-5 times the center frequency or higher, and repeated acquisitions are taken at a frame rate of at least twenty frames per second.

The processed ultrasound data will be assembled into conventional B-mode images 38 providing a real-time representation of a plane through the uterus 18 according to well-known techniques. Further processing, according to the present invention (as will be described below), may be performed by a processor 33 executing a stored program contained in memory 35 residing either in the standard ultrasonic imaging system 10 or the stand-alone computer 30.

Figure 2:
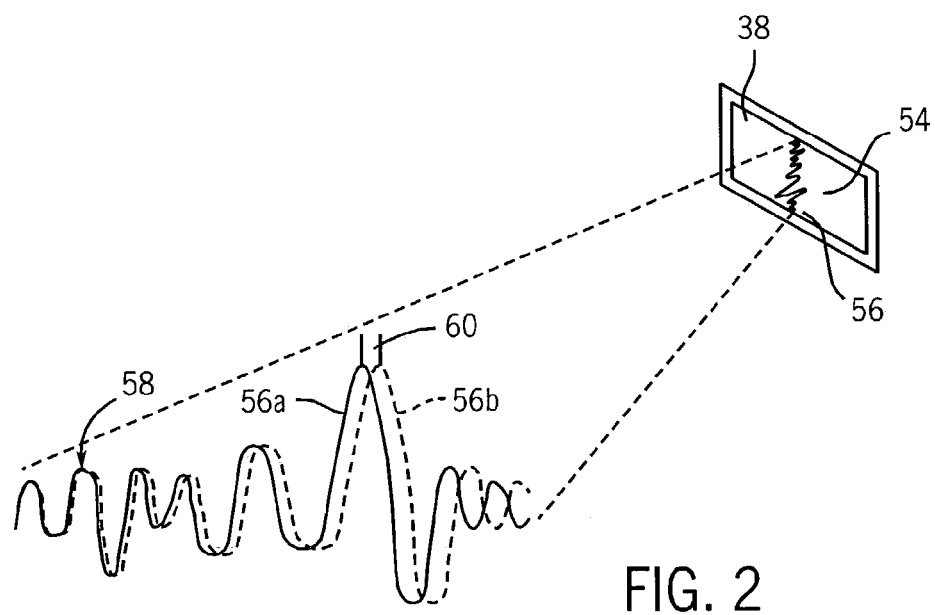
FIG. 2 is a graphical representation of an ultrasonic signal received by the ultrasound scanner of FIG. 1 showing the analysis of one waveform of the signal taken at two successive times with a different strain of the uterine tissue showing a shifting of the signals corresponding to such strain.

Referring now also to FIG. 2, each B-mode image 38 is composed of a series of time-domain signals 56 corresponding approximately with the rays 16, and having a varying amplitude mapped to brightness of pixels 54 forming the columns of the B-mode image 38. As such, the time axis of each signal 56 generally reflects distance from the ultrasound transducer 12 to the tissue of the uterus 18.

The strain within the tissue of the uterus 18 may be determined by comparing corresponding time-domain signals 56a and 56b from two sequential ultrasound echo B-mode images 38 measuring the uterine tissue at different degrees of displacement (e.g., compression or distention) as will be described below. As shown, the second time-domain image signal 56b exhibits an expansion in time reflecting an expansion or distention of the uterine tissues toward or away from the ultrasound transducer 12. More generally, the later time-domain image signal 56b might represent either relative distention or relative compression with respect to earlier time-domain image signal 56a.

A general translation of the tissue of the uterus 18 (rather than local compression or distention) would cause an equal offset between all points in time-domain image signals 56a and 56b. However, the elasticity of the tissue causes local tissue compression or distention, which in turn produces a gradient in the phase offset of the time-domain image signals 56a and 56b as a function of time and distance from the ultrasound transducer 12.

For the example shown, the phase offset 58 between the time-domain image signals 56a and 56b at early times and hence near the ultrasound transducer 12 will be smaller than the phase offset 60 at later times and for tissue further away from the ultrasound transducer 12. The rate of change of these displacements at points over the region of the uterus 18 provides a series of strain values having magnitude and sign that is used to produce an elastographic image of the tissue of the uterus 18.

Referring to FIG. 3 more specifically, ultrasonic radio frequency (RF) scan data 64 is collected being at least two B-mode images 38 containing successive time-domain image signals 56a and 56b. At process block 65, these signals are processed to determine tissue displacement along an axis from the ultrasound transducer 12 through the uterus 18. In principle, short segments of the time-domain image signals 56a and 56b are analyzed by moving one segment with respect to the other until a best match is obtained and the amount of movement needed for the best match determines tissue displacement. The matching process may be implemented by means of mathematical correlation of the segments.

The displacement of signal 66 output by process block 65 is further processed by the process block 68, which determines strain as a gradient of the displacement signal. The strain values 71 may be mapped to an elastographic image 72.

As each successive frame is obtained by the system of FIG. 1, a new elastographic image 72 may be obtained by comparing that frame to the predecessor frame to determine displacement as has been described, and thus the strain is relative to the last B-mode image 38. Alternatively, a base image approximating the uterus 18 uncompressed or at an initial state of compression may be used to produce an elastographic image 72 relative to that base image. More generally a peak or root-mean-square value or other similar measure can be adopted for computing strain.

Referring momentarily to FIG. 4, alternative algorithms may be used to create the elastographic images 72. In one such algorithm, the time-domain image signals 56a and 56b may be received by process block 81 to extract spectra of the time-domain image signals 56a and 56b using, for example, the well-known fast Fourier transform algorithm. The spectra of the time-domain image signals 56a and 56b will be shifted according to the Fourier transformation property that causes dilation in a time-domain signal to produce a down-frequency shift in its frequency-domain spectrum. The amount of shift may be determined at process block 83 using correlation techniques similar to those used in process block 65 but executed on the frequency-domain signals.

The shift between the spectra taken of different segments of the time-domain signals 56a and 56b, centered at increasing time delays, provides a gradient signal to produce elastographic images 72. While the results are similar to the technique of FIG. 3, this approach may have some advantages in terms of robustness against noise and the like.

Each of these process blocks may be implemented through a combination of hardware and software in the ultrasonic imaging system 10 and/or the stand-alone computer 30 as is well understood to those of ordinary skill in the art.

Referring now to FIGS. 3 and 5, the strain values 71 for each pixel 74 of the elastographic images 72 will have a magnitude and sign. The magnitude indicates the amount of the distension or compression of the tissue and the sign indicates whether it is a compression or distention with positive signs normally denoting compression and negative signs by convention noting distension of the tissue. These values may be mapped to colors and displayed in an elastographic image 72. The elastographic image is that which will be used for detection of tumors or the like.

Referring now to FIGS. 1 and 5, the processor 33 executing the stored program in memory 35 may juxtapose the conventional B-mode image 38 (typically in a gray scale) next to the elastographic image 72 on the display 32. The B-mode image 38 shows relatively time invariant qualities of the uterine tissue, such as tissue interfaces, and further provides a higher resolution image of the uterus 18 in which anatomical features may be more readily distinguished. The B-mode images 38 and elastographic image 72 may be static or updated in real time and sized and oriented to show the same region of uterine tissue.

The program may also provide for a cursor 80 that may be positioned over the B-mode images 38 and a cursor 82 that may be positioned over the elastographic image 72, respectively, through the use of the cursor control device 36 and keyboard 34. Cursor 80 and 82, in any case, are positioned to track each other so as to constantly contain a region of interest 84 centered on the same structure in both the B-mode images 38 and elastographic image 72. In this manner, the B-mode image 38 may be used to identify particular anatomy of the uterus 18, for example, the cervix 104 and the strain may be investigated locally by reviewing the region within the cursor 82.

A quantitative readout 86 may be provided on the graphic display 32 providing statistics related to the strain of tissue contained in the region of interest of the cursor 82. In the simplest embodiment, a current average strain relative to the last B-mode image 38 may be displayed or alternatively a peak strain, absolute strain, or average strain magnitude may be displayed. For evaluation of cervical incompetence, the data acquired with the cursor 82 on the cervix 104 may be compared to empirically obtained data representing values for a standard population having known cervical function and the measured data displayed in chart form 90 providing a marker 93 displaying a qualitative indication of how the patient compares to a characterized standard population.

Figures 6, 7, 8:
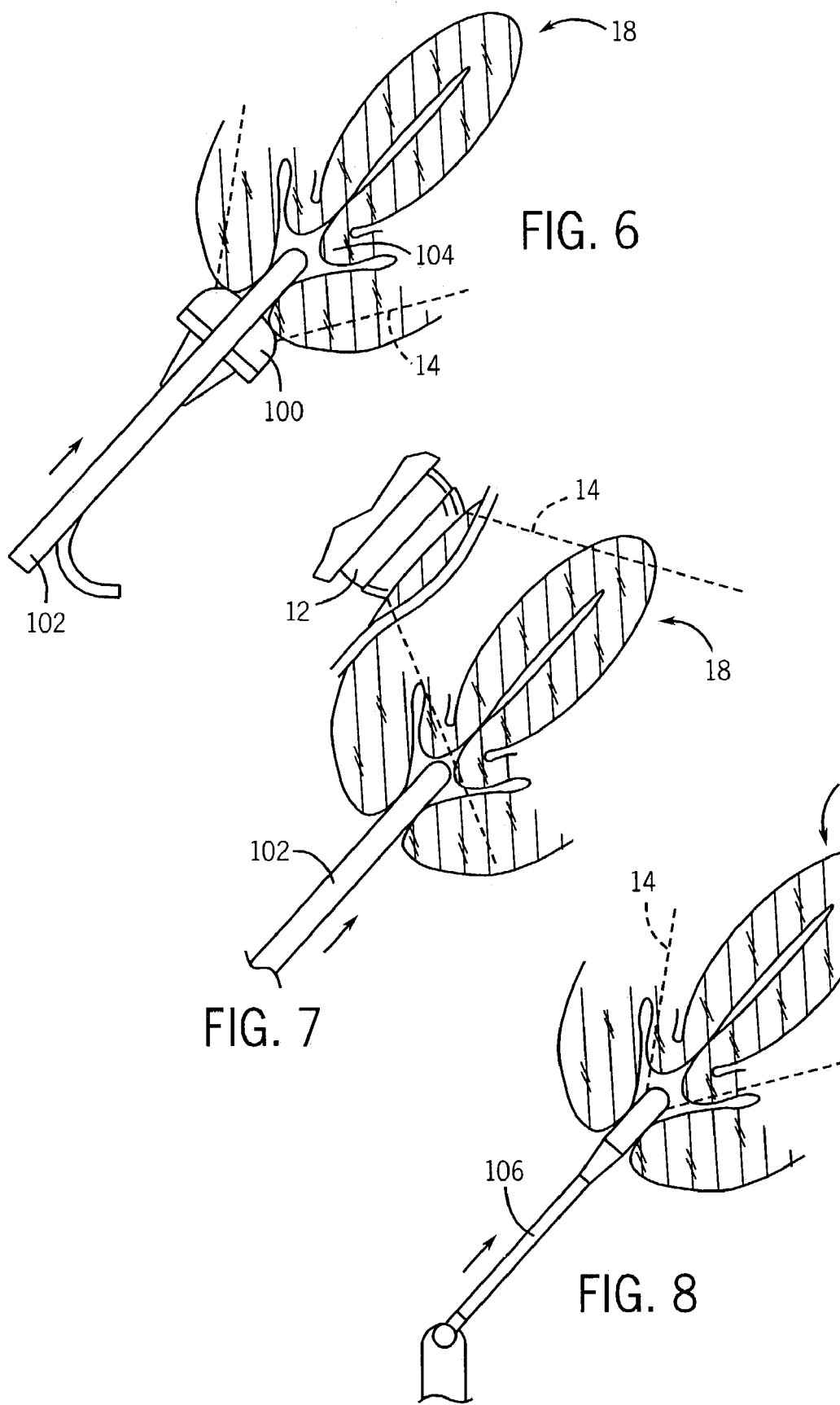
FIG. 6 is a cross section of a patient taken along a mid-sagittal plane of the uterus and perineal area showing the use of a transperineal ultrasound probe together with a blunt probe for displacement of the tissue of the cervix.
FIG. 7 is a figure similar to that of FIG. 6 showing the use of a blunt of probe of FIG. 6 with a transabdominal ultrasonic probe.
FIG. 8 is figure similar to that of FIGS. 6 and 7 showing the use of a transvaginal probe both for ultrasonic acquisition and for tissue displacement.

Referring now to FIG. 6, in a first data collection method, a transperineal ultrasonic probe 100 may be directed toward the uterus 18 so that its rays 16 illuminate the uterus 18 from an inferior direction. A mechanical probe 102, for example a blunt rod, may then be used to apply compression to the cervix 104 in between acquisition of B-mode images 38.

Referring to FIG. 7 in an alternative acquisition technique, a transabdominal ultrasound transducer 12 may be directed to illuminate the uterus 18 from the abdomen, again with the mechanical probe 102 used to provide the necessary tissue displacement.

Referring to FIG. 8, alternatively, a transvaginal ultrasonic probe 106 may illuminate the uterus 18 from the inferior direction and may fit within the vagina to apply compression directly to the cervix 104 in place of the mechanical probe 102 as previously described.

In each of these techniques the operator may provide a signal to the ultrasonic imaging system 10 through the keyboard 34 or the like indicating a command to obtain additional B-mode image 38 with displacement and without displacement. This command could also be derived from a sensor that detects or measures the motions of probe 102. Alternatively, the elastographic images 72 may be generated on a real-time basis as displacement is applied.

Figure 9:
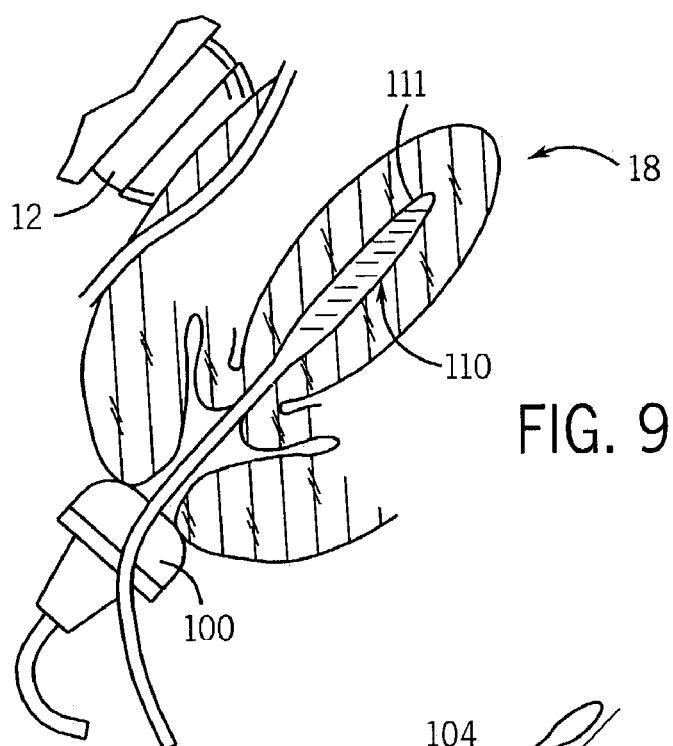
FIG. 9 is a figure similar to that of FIGS. 6-8 showing the use of a transabdominal ultrasonic probe or a transperineal probe with a balloon for displacement of the uterine tissue.
Figure 10:
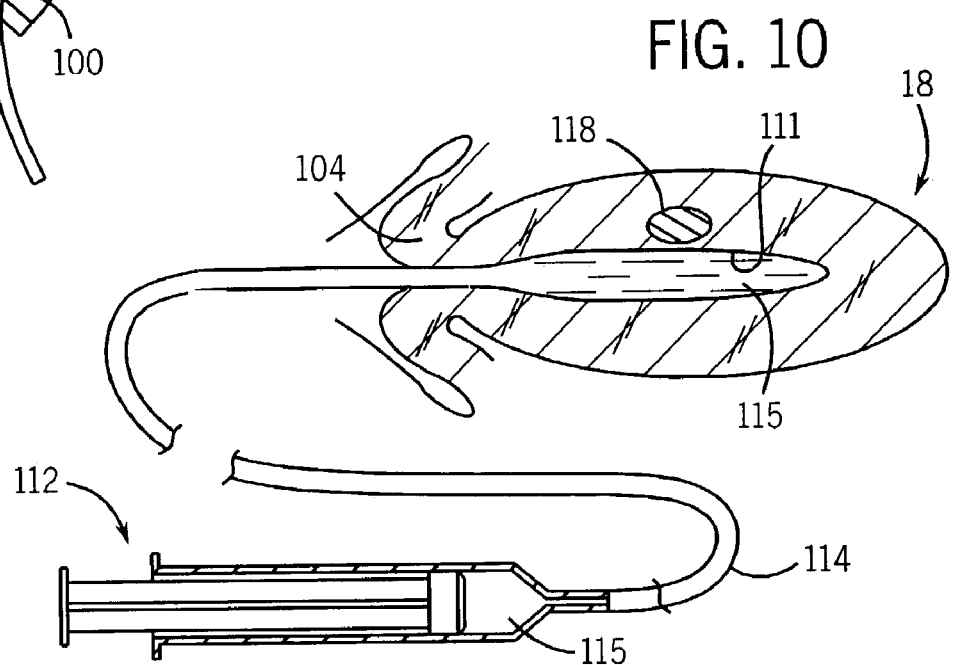
FIG. 10 is a detailed view of the uterus of FIG. 9 showing the use of a syringe for inflation and deflation of the balloon placed within the uterus adjacent to an unknown mass.

Referring now to FIGS. 9 and 10 displacement of the tissue of the uterus 18 as a whole, as opposed to only the tissue of the cervix 104, may be accomplished through the use of a balloon-end catheter 110 having a balloon 111 sized to extend substantially the length of the uterus 18. The balloon 111 of the balloon-end catheter 110 is inserted within the uterus and a first image is obtained. The balloon portion may then be inflated with a saline solution 115 to press outward on the muscle wall of the uterus 18 by using a simple pump 112 such as a syringe attached to tubing 114 connecting to the balloon 111 of the balloon-end catheter 110. Alternatively multiple images may be taken of different degrees of inflation of the balloon 111.

Referring to FIG. 9, the displacement caused by the balloon 111 may be imaged either using a transabdominal ultrasound transducer 12 or the transperineal ultrasonic probe 100 or the transvaginal ultrasonic probe 106 (the latter shown in FIG. 8). It is believed that the displacement will reveal a strain image that may identify localized masses 118 having a stiffness that differs from the general muscle of the uterus 18 which will be apparent in the elastographic image 72 of FIG. 5.

Referring now to FIG. 15, displacement of the tissue of the vagina 140 as a whole, as opposed to only the tissue of the uterus 18 or cervix 104, may be accomplished through the use of a balloon-end catheter 142 having a balloon 143 sized to extend substantially the length of the vagina 140. The balloon 143 of the balloon-end catheter 142 is inserted within the vagina 140 and a first image is obtained. The balloon 143 may then be inflated with a saline solution as described above and a second image obtained. Alternatively multiple images may be taken of different degrees of inflation of the balloon 143.

The displacement caused by the balloon 143 may be imaged either using a transabdominal ultrasound transducer 12 or the transperineal ultrasonic probe 100 or the transvaginal ultrasonic probe 106 (the latter shown in FIG. 8) or intravascular ultrasound transducer 128 within the balloon 143 as described above. It is believed that the displacement will reveal a strain image that may identify localized defects having a stiffness that differs from the intact fibromuscular sheath investing the vagina, which will be apparent in the elastographic image. Alternatively, the displacement of the vagina 140 may be done using a mechanical probe 102 or the transvaginal ultrasonic probe 106 as described above.

Figure 11:
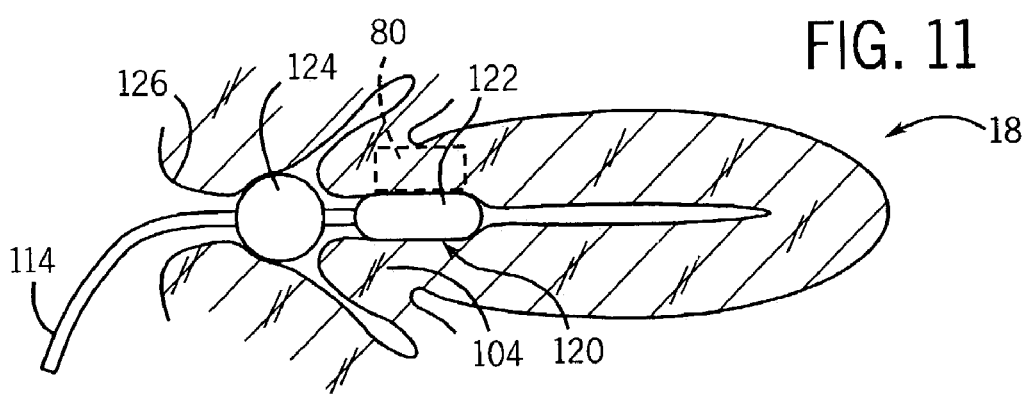
FIG. 11 is a figure similar to that of FIG. 10 showing a smaller balloon for use in displacement of only the cervix as anchored by a secondary balloon and showing a region of interest for cervical characterization.

Referring now to FIG. 11, a dual-balloon catheter 120 may also be used for cervical measurements having a first balloon 122 at one end of the catheter and sized to extend only through the cervix 104 of the uterus 18. Positioning of the balloon 122 may be provided by a second balloon 124 removed from the first end that may be inflated in the vaginal canal 126 outside of the cervix 104, or alternatively with a balloon (not shown) held within the uterus 18 itself. For these measurements, the cursor 80 will be placed on the wall of the cervix 104 to make the necessary composite strain measurements as may be then related to the population at large.

Figure 12:
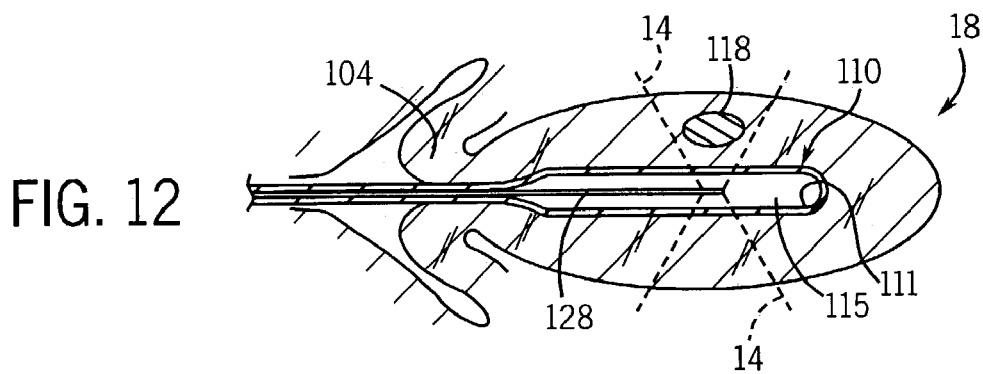
FIG. 12 is a view similar to that of FIG. 10 showing a balloon surrounding a side-looking ultrasonic probe for scanning the uterus while moving within the balloon.

Referring now to FIG. 12, in a further embodiment, a thin intravascular ultrasound transducer 128 is inserted within the balloon 111 to provide a radial or side-looking beam 14 that may scan the uterus 18 from within the balloon 111 of the balloon-end catheter 110. This scanning may be performed by rotation of the thin ultrasound transducer 128 about long axis accompanied by translation of the thin ultrasound transducer 128 along its axis. In this way, a composite image of the uterus 18 may be collected on a slice-by-slice basis. Alternatively, the thin ultrasound transducer 128 may be directed manually by the physician to scan the uterus 18 looking for particular elastographic anomalies on a real time display of elastographic images 72. The saline solution 115 provides a coupling of the ultrasound from the intravascular ultrasound transducer 128 into the tissue of the uterus 18.

Figure 13:
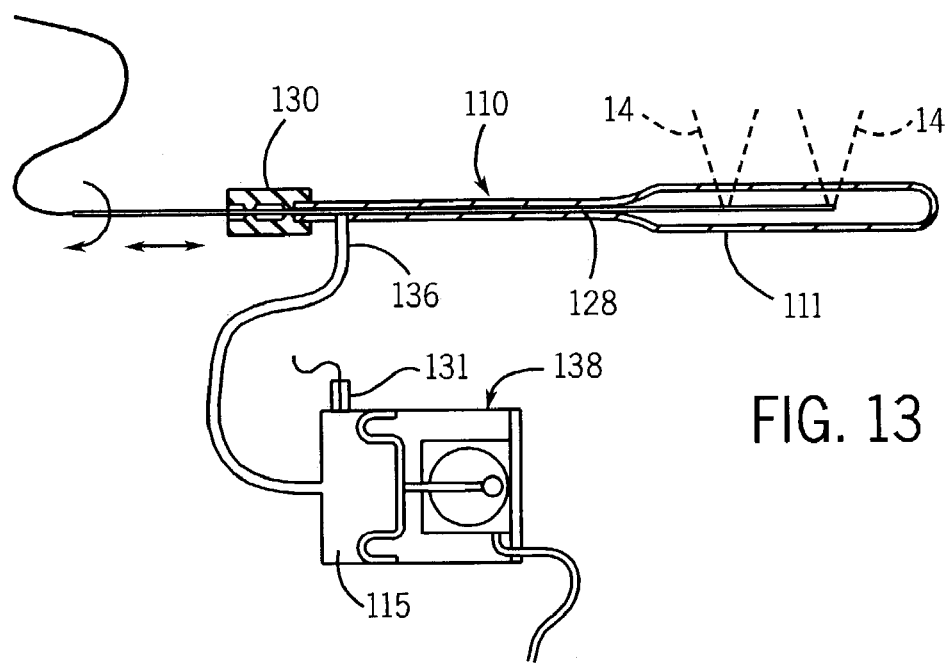
FIG. 13 is a simplified cross sectional view of a probe system providing for inflation of a balloon and independent axial movement over the ultrasonic probe of FIG. 12.
Figure 14:
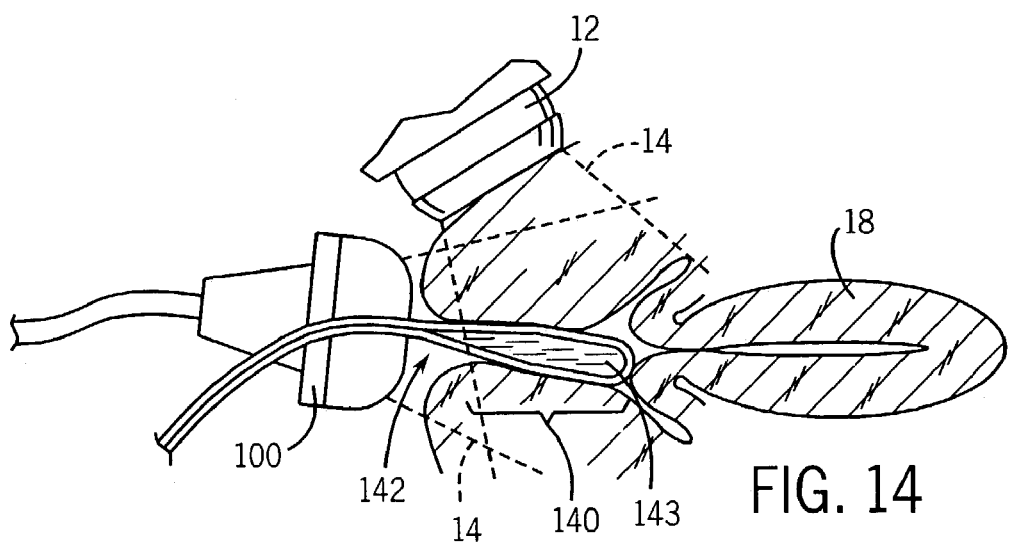
FIG. 14 is a figure similar to that of FIGS. 10 and 11 showing an embodiment of the balloon for placement in the vagina for measurement of the tissue of the pelvic floor.

Referring to FIG. 13, for the above scanning, the balloon-end catheter 110 may include a seal 130 opposed to the balloon 111 removed from the patient. The shaft of the intravascular ultrasound transducer 128 may exit through the seal 130, which allows a translation and rotation of the intravascular ultrasound transducer 128 without loss of saline solution 115.

A T-connection 136 may connect the lumen of the balloon-end catheter 110 to an electric pump 138 providing for a periodic sinusoidal inflation and deflation of the balloon 111 of the balloon-end catheter 110. Electric pump 138 may be, for example, a rolling diaphragm pump attached through a crank arm to a rotation motor or the like. A separate syringe (not shown) may be used to adjust the mean inflation. A signal may pass from the pump 138 to be received by the ultrasonic imaging system 10 to coordinate its acquisition of images during the deflation and inflation portion of the pump cycles. In this way repeated measurements may be made during the scanning process. A pressure transducer 131 may provide an instantaneous measure of balloon pressure. This pressure measurement allows better reproducibility of the elasticity measurements and/or may allow quantitative measurements such as Young's modulus to be made using appropriate boundary conditions.

In one embodiment of the invention, the pump communicating with the balloons described above will be used to apply cyclical or dynamic compression and relaxation at a low frequency (inflation and deflation with saline). Imaging will then be performed transabdominally using tissue Doppler or Tissue Velocity Imaging, to obtain strain and strain rate images, using a scanner such as a GE Vingmed Vivid 5 or Vivid 7 scanner (commercially available from GE Vingmed of Forton, Norway)

The present invention is applicable to a range of specific techniques for measurement of tissue elasticity including but not limited to Sonoelasticity or Sonoelastography, Dynamic Elastography, MRI elastography any of which may be used to estimate strain, strain rate or Young's Modulus images all of which should be considered measures of elasticity for the purpose of this application. It is specifically intended that the present invention not be limited to the embodiments and illustrations contained herein, but include modified forms of those embodiments including portions of the embodiments and combinations of elements of different embodiments as come within the scope of the following claims.

We claim:

1. A method for evaluating cervical incompetence comprising the steps of:
   (a) obtaining a first image of the cervix with an ultrasonic acoustic wave;
   (b) applying displacement to the cervix;
   (c) obtaining a second image of the cervix to deduce elasticity of the cervix under the displacement; and
   (d) outputting a measurement based on the deduced elasticity indicating a likelihood of cervical incompetence.

2. The method of claim 1 wherein the first and second images are obtained using an ultrasonic acoustic wave transmitted by an ultrasonic probe, a portion of which also applies the displacement.

3. The method of claim 1 wherein the first and second images are obtained using an ultrasonic probe and the displacement is applied with a second non-transmitting probe.

4. The method of claim 3 wherein the ultrasonic probe is applied transvaginally.

5. The method of claim 3 wherein the ultrasonic probe is applied transabdominally.

6. The method of claim 1 wherein the displacement is applied by inflation of a balloon within the cervix.

7. The method of claim 6 and the first and second images are obtained transabdominally using an ultrasonic probe positioned on the abdomen.

8. The method of claim 6 and the first and second images are obtained transperineally using an ultrasonic probe positioned at the perineum.

9. The method of claim 6 and the first and second images are obtained using an ultrasonic probe positioned within the balloon.

10. The method of claim 1 wherein the output is an image of the cervix indicating variations in elasticity within the cervix.

11. The method of claim 1 wherein the output is a quantitative measure of elasticity of the cervix.

12. The method of claim 1 including the step of comparing the elasticity of the cervix with a threshold elasticity deduced from a standard population and wherein the output is a result of this comparison.

13. The method of claim 1 including the step of defining an area of the cervical tissue and combining elasticity measurements over that area, and wherein the output is the combination of the elasticity measurements.

14. An apparatus for evaluating cervical incompetence comprising:
   an ultrasound transducer for receiving an ultrasonic acoustic signal passing through cervical tissue;
   ultrasonic processing circuitry communicating with the ultrasound transducer and producing an image from the ultrasonic acoustic signals received thereby;
   a compressor, for compressing the cervix;
   an electronic computer communicating with the ultrasound transducer and executing a stored program to:
      (i) obtain a first image of the cervix;
      (ii) provide an output signaling a time during which the cervix should be compressed;
      (iii) obtain a second image of the cervix during the displacement;
      (iv) process the first and second images to determine elasticity of the cervical tissue; and
      (v) compare the elasticity to a stored model to provide an indication of the likelihood of cervical incompetence.

15. A method for detecting tumors in the uterine wall comprising the steps of:
   (a) directing an ultrasonic probe to obtain a first image of the uterine wall with an ultrasonic acoustic wave passing through the uterine wall;
   (b) applying displacement to the uterine wall by inflating the uterus with an ultrasonically conductive liquid;
   (c) obtaining a second image of the uterine wall to deduce elasticity of the uterine wall under the displacement; and
   (d) comparing the first and second images to determine strain in the tissue of the uterine wall from a gradient of displacement of the tissue between the first and second images;
   (d) outputting an image of the uterine wall indicating variations in elasticity of the uterine wall based on the strain and associated with tumorous tissue.

16. The method of claim 15 wherein the ultrasonic probe is applied transvaginally.

17. The method of claim 15 wherein the ultrasonic probe is applied transabdominally.

18. The method of claim 15 and the first and second images are obtained transabdominally using an ultrasonic probe positioned on the abdomen.

19. The method of claim 15 and the first and second images are obtained transperineally using an ultrasonic probe positioned at the perineum.

20. The method of claim 15 and the first and second images are obtained using an ultrasonic probe positioned within the balloon.

21. The method of claim 15 wherein the output is a quantitative measure of elasticity of the uterus.

22. The method of claim 15 including the step of comparing the elasticity of the uterus with a threshold elasticity deduced from a standard population and wherein the output is a result of this comparison.

23. The method of claim 15 including the step of defining an area of the uterine tissue and combining elasticity measurements over that area, and wherein the output is the combination of the elasticity measurements.

24. The method of claim 15 wherein the displacement is applied by inflation of a balloon within the vagina.

25. The method of claim 24 and the first and second images are obtained transabdominally using an ultrasonic probe positioned on the abdomen.

26. The method of claim 24 and the first and second images are obtained transperineally using an ultrasonic probe positioned at the perineum.

27. The method of claim 24 and the first and second images are obtained using an ultrasonic probe positioned within the balloon.

28. An apparatus for evaluating cervical incompetence comprising:
    an ultrasound transducer for receiving an ultrasonic acoustic signal passing through cervical tissue;
    an ultrasonic processing circuitry communicating with the ultrasound transducer and producing an image from the ultrasonic acoustic signals received thereby;
    a compressor, for compressing the cervix;
    an electronic computer communicating with the ultrasound transducer and executing a stored program to:
       (i) obtain a first image of the cervix;
       (ii) provide an output signaling a time during which the cervix should be compressed;
       (iii) obtain a second image of the cervix during the displacement;
       (iv) process the first and second images to determine elasticity of the uterine tissue; and
       (v) compare the elasticity to a stored model to provide an indication of likelihood of cervical incompetence.

29. A method for evaluating pelvic floor incompetence comprising the steps of:
    (a) obtaining a first image of the vaginal wall with an ultrasonic acoustic wave;
    (b) applying displacement to the vaginal wall;
    (c) obtaining a second image of the vaginal wall to deduce elasticity of the vaginal wall under the displacement; and
    (d) compare the elasticity to a stored model to output an indication of likelihood of pelvic floor incompetence.

30. The method of claim 29 wherein the first and second images are obtained using an ultrasonic acoustic wave transmitted by an ultrasonic probe, a portion of which also applies the displacement.

31. The method of claim 29 wherein the first and second images are obtained using an ultrasonic probe and the displacement is applied with a second non-transmitting probe.

32. The method of claim 31 wherein the ultrasonic probe is applied transvaginally.

33. The method of claim 31 wherein the ultrasonic probe is applied transabdominally.

34. The method of claim 29 wherein the output includes an image of the vaginal wall indicating variations in elasticity within the vaginal wall.

35. The method of claim 29 wherein the output includes a quantitative measure of elasticity of the vaginal wall.

36. The method of claim 29 wherein the stored model is with a threshold elasticity deduced from a standard population and wherein the output is a result of this comparison.

37. The method of claim 29 including the step of defining an area of the vaginal wall sheath and combining elasticity measurements over that area, and wherein the output employs the combination of the elasticity measurements.

38. An apparatus for evaluating pelvic floor incompetence comprising:
    an ultrasound transducer for receiving an ultrasonic acoustic signal passing through vaginal wall tissue;
    an ultrasonic processing circuitry communicating with the ultrasound transducer and producing an image from the ultrasonic acoustic signals received thereby;
    a compressor, for compressing the vaginal wall;
    an electronic computer communicating with the ultrasound transducer and executing a stored program to:
       (i) obtain a first image of the vaginal wall;
       (ii) provide an output signaling a time during which the vaginal wall should be compressed;
       (iii) obtain a second image of the vaginal wall during the displacement;
       (iv) process the first and second images to determine elasticity of the vaginal wall tissue; and
       (v) compare the elasticity to a stored model to provide an indication of likelihood of pelvic floor incompetence.

* * * * *